US012745981B2

(12) United States Patent
Lee et al.

(10) Patent No.: US 12,745,981 B2
(45) Date of Patent: *Sep. 29, 2026

(54) ULTRASOUND SYSTEM AND SIGNAL PROCESSING UNIT CONFIGURED FOR TIME GAIN AND LATERIAL GAIN COMPENSATION

(71) Applicant: Samsung Medison Co., Ltd., Gangwon-do (KR)

(72) Inventors: Doo Sik Lee, Seoul (KR); Mi Jeoung Ahn, Seoul (KR)

(73) Assignee: SAMSUNG MEDISON CO., LTD., Gangwon-Do (KR)

( * ) Notice: Subject to any disclaimer, the term of this patent is extended or adjusted under 35 U.S.C. 154(b) by 0 days.

This patent is subject to a terminal disclaimer.

(21) Appl. No.: 18/981,191

(22) Filed: Dec. 13, 2024

(65) Prior Publication Data

US 2025/0107777 A1 Apr. 3, 2025

Related U.S. Application Data

(63) Continuation of application No. 18/138,334, filed on Apr. 24, 2023, now Pat. No. 12,193,879, which is a (Continued)

(30) Foreign Application Priority Data

Dec. 7, 2006 (KR) ........................ 10-2006-0123752

(51) Int. Cl.
*A61B 8/00* (2006.01)
*A61B 8/14* (2006.01)
(Continued)

(52) U.S. Cl.
CPC ................ *A61B 8/467* (2013.01); *A61B 8/00* (2013.01); *A61B 8/14* (2013.01); *A61B 8/4254* (2013.01);
(Continued)

(58) Field of Classification Search
CPC .. A61B 8/467; A61B 8/00; A61B 8/14; A61B 8/4254; A61B 8/4444; A61B 8/46;
(Continued)

(56) References Cited

U.S. PATENT DOCUMENTS 4,043,181 A 8/1977 Nigam
4,475,400 A 10/1984 Flax
(Continued)

FOREIGN PATENT DOCUMENTS

EP 0 539 697 A1 5/1993
EP 1 219 972 A2 7/2002
(Continued)

OTHER PUBLICATIONS

U.S. Non-Final Office Action dated Aug. 7, 2017 issued in U.S. Appl. No. 13/756,274.

(Continued)

*Primary Examiner* — Sanjay Cattungal
(74) *Attorney, Agent, or Firm* — Morgan Lewis & Bockius LLP

(57) ABSTRACT

The present invention provides an ultrasound system, which comprises: a signal acquiring unit to transmit an ultrasound signal to an object and acquire an echo signal reflected from the object; a signal processing unit to control TGC (Time Gain Compensation) and LGC (Lateral Gain Compensation) of the echo signal; a TGC/LGC setup unit adapted to set TGC and LGC values based on TGC and LGC curves inputted by a user; and an image producing unit adapted to produce an ultrasound image of the object based on the echo signal. The signal processing unit is further adapted to control the TGC and the LGC of the echo signal based on the TGC and LGC values set by the TGC/LGC setup unit.

17 Claims, 8 Drawing Sheets

Related U.S. Application Data continuation of application No. 17/723,111, filed on Apr. 18, 2022, now Pat. No. 11,633,174, which is a continuation of application No. 15/945,313, filed on Apr. 4, 2018, which is a continuation of application No. 13/756,274, filed on Jan. 31, 2013, now Pat. No. 10,321,891, which is a continuation of application No. 13/184,094, filed on Jul. 15, 2011, now Pat. No. 8,403,855, which is a continuation of application No. 11/857,860, filed on Sep. 19, 2007, now Pat. No. 8,016,759.

(51) Int. Cl.

*G01S 7/52* (2006.01)
*G06F 3/01* (2006.01)
*G06F 3/048* (2013.01)
*G06F 3/0484* (2022.01)
*G06F 3/04845* (2022.01)
*G06F 3/04847* (2022.01)
*G06T 7/00* (2017.01)
*A61B 6/46* (2024.01)

(52) U.S. Cl.

CPC .............. *A61B 8/4444* (2013.01); *A61B 8/46* (2013.01); *A61B 8/461* (2013.01); *A61B 8/462* (2013.01); *A61B 8/463* (2013.01); *A61B 8/465* (2013.01); *A61B 8/5207* (2013.01); *A61B 8/5269* (2013.01); *A61B 8/54* (2013.01); *G01S 7/52033* (2013.01); *G01S 7/52084* (2013.01); *G06F 3/01* (2013.01); *G06F 3/048* (2013.01); *G06F 3/0484* (2013.01); *G06F 3/04845* (2013.01); *G06F 3/04847* (2013.01); *G06T 7/0012* (2013.01); *A61B 6/467* (2013.01)

(58) Field of Classification Search

CPC ......... A61B 8/461; A61B 8/462; A61B 8/463; A61B 8/465; A61B 8/5207; A61B 8/5269; A61B 8/54; A61B 6/467; G01S 7/52033; G01S 7/52084; G01S 5/18; G06F 3/01; G06F 3/048; G06F 3/0484; G06F 3/04845; G06F 3/04847; G06T 7/0012; G01N 29/24

See application file for complete search history.

(56) References Cited

U.S. PATENT DOCUMENTS 4,817,614 A 4/1989 Hassler et al.
5,161,535 A 11/1992 Short et al.
5,245,586 A 9/1993 Hassler
5,257,624 A 11/1993 Fraser
5,265,612 A 11/1993 Sarvazyan
5,315,999 A 5/1994 Kinicki et al.
5,482,045 A 1/1996 Rust et al.
5,524,636 A 6/1996 Sarvazyan
5,606,971 A 3/1997 Sarvazyan
5,678,565 A 10/1997 Sarvazyan
5,810,731 A 9/1998 Sarvazyan
5,993,392 A 11/1999 Roundhill
6,063,030 A 5/2000 Vara et al.
6,099,471 A 8/2000 Torp
6,102,859 A * 8/2000 Mo .......................... A61B 8/00 600/443
6,142,942 A 11/2000 Clark
6,261,234 B1 7/2001 Lin
6,368,279 B1 4/2002 Liu
6,373,970 B1 * 4/2002 Dong ................. G06V 10/7515 382/280
6,423,004 B1 * 7/2002 Dong .................. G01S 7/52069 600/443
6,468,212 B1 10/2002 Scott et al.
6,494,834 B2 12/2002 Konofagou et al.
6,517,485 B2 2/2003 Torp
6,579,238 B1 * 6/2003 Simopoulos ........ G01S 15/8988 600/443
6,592,520 B1 * 7/2003 Peszynski ................ A61B 8/12 600/459
6,677,985 B1 1/2004 Kubota et al.
6,933,934 B2 8/2005 Amemiya
7,022,075 B2 4/2006 Grunwald et al.
8,016,759 B2 9/2011 Lee et al.
8,235,898 B2 8/2012 Bae
8,403,855 B2 3/2013 Lee et al.
9,072,471 B2 7/2015 Kato
9,314,225 B2 4/2016 Steen
10,456,111 B2 10/2019 Lee
10,517,572 B2 12/2019 Kang
11,020,091 B2 6/2021 Jin
2002/0008692 A1 1/2002 Omura et al.
2002/0087218 A1 7/2002 Amemiya
2003/0028107 A1 * 2/2003 Miller .................. A61B 5/6819 600/437
2003/0097071 A1 5/2003 Halmann et al.
2003/0187353 A1 10/2003 Ng et al.
2003/0195418 A1 10/2003 Barnes
2003/0236459 A1 12/2003 Loftman et al.
2004/0015079 A1 1/2004 Berger et al.
2005/0049497 A1 3/2005 Krishnan
2005/0059892 A1 3/2005 Dubois et al.
2005/0085730 A1 4/2005 Flesch
2006/0020204 A1 1/2006 Serra
2006/0025682 A1 2/2006 Vanderby
2006/0052696 A1 3/2006 Shiina
2007/0083116 A1 4/2007 Sato
2007/0112270 A1 5/2007 Waki
2007/0230759 A1 * 10/2007 Tamura ............... G01S 7/52033 382/128
2007/0239019 A1 10/2007 Richard et al.
2008/0081994 A1 4/2008 Kim
2008/0119732 A1 5/2008 Hiltawsky
2008/0170765 A1 * 7/2008 D'sa ...................... A61B 8/467 382/128
2008/0287792 A1 11/2008 Bae
2008/0306385 A1 * 12/2008 Jago .................... G01S 7/52098 600/443
2009/0043195 A1 2/2009 Poland
2009/0069677 A1 3/2009 Chen et al.
2009/0076387 A1 3/2009 Simopoulos
2009/0124903 A1 5/2009 Osaka
2009/0131797 A1 5/2009 Jeong
2009/0182234 A1 7/2009 Perrey
2009/0326378 A1 12/2009 Lee
2010/0049050 A1 2/2010 Pelissier
2010/0145195 A1 6/2010 Hyun
2010/0217128 A1 8/2010 Betts
2010/0220901 A1 9/2010 Matsumura
2010/0292572 A1 11/2010 Simpson
2011/0043434 A1 2/2011 Roncalez et al.
2011/0054325 A1 3/2011 Shin et al.
2011/0071395 A1 * 3/2011 Miller ................. G01S 7/52063 600/440
2012/0133601 A1 5/2012 Marshall
2013/0030298 A1 1/2013 Tamura
2013/0064036 A1 3/2013 Lee et al.
2013/0144169 A1 6/2013 Lee et al.
2013/0226001 A1 8/2013 Steen
2013/0239052 A1 9/2013 Moody
2013/0249842 A1 9/2013 Varna
2013/0324850 A1 12/2013 Petruzzelli
2014/0088428 A1 3/2014 Yang et al.
2014/0164965 A1 6/2014 Lee et al.
2014/0243669 A1 8/2014 Halmann
2015/0121277 A1 4/2015 Yoon
2016/0007965 A1 1/2016 Murphy
2016/0120508 A1 5/2016 Kim
2016/0139789 A1 5/2016 Jin et al.

(56) References Cited

U.S. PATENT DOCUMENTS

FOREIGN PATENT DOCUMENTS

| | | | |
|---|---|---|---|
| JP | H06-154227 | A | 6/1994 |
| JP | 10-248843 | A | 9/1998 |
| JP | 2000-197637 | A | 7/2000 |
| JP | 2006-296978 | A | 11/2006 |
| KR | 10-2001-0067091 | A | 7/2001 |
| KR | 10-2004-0069378 | A | 8/2004 |
| KR | 2006-0033845 | A | 4/2006 |
| WO | 2016/060475 | A1 | 4/2016 |

OTHER PUBLICATIONS

U.S. Office Action dated May 4, 2017 issued in U.S. Appl. No. 13/586,290.
U.S. Final Office Action dated Aug. 12, 2016 issued in U.S. Appl. No. 13/756,274.
U.S. Office Action dated Oct. 8, 2013 issued in U.S. Appl. No. 13/938,847.
U.S. Final Office Action dated Mar. 13, 2014 issued in U.S. Appl. No. 13/475,686.
U.S. Office Action dated Mar. 21, 2014 issued in U.S. Appl. No. 13/938,847.
U.S. Office Action dated Mar. 26, 2015 issued in U.S. Appl. No. 13/475,686.
U.S. Non-Final Office Action dated Jul. 17, 2015 issued in U.S. Appl. No. 13/586,290.
U.S. Office Action dated Jun. 10, 2015 issued in U.S. Appl. No. 13/938,847.
U.S. Non-Final Office Action dated Jan. 5, 2016 issued in U.S. Appl. No. 14/866,038.
U.S. Office Action dated Mar. 3, 2016 issued in U.S. Appl. No. 13/586,290.
U.S. Office Action dated Jul. 1, 2016 issued in U.S. Appl. No. 14/866,038.
U.S. Office Action dated Aug. 2, 2013 issued in U.S. Appl. No. 13/475,686.
U.S. Non-Final Office Action dated Feb. 26, 2016 issued in U.S. Appl. No. 13/756,274.
U.S. Final Office Action dated Mar. 3, 2022 issued in U.S. Appl. No. 15/945,313.
U.S. Non-Final Office Action dated Aug. 25, 2021 issued in U.S. Appl. No. 15/945,313.
U.S. Final Office Action dated Jan. 7, 2021 issued in U.S. Appl. No. 15/945,313.
U.S. Non-Final Office Action dated Jun. 26, 2020 issued in U.S. Appl. No. 15/945,313.
U.S. Office Action dated Nov. 22, 2022 issued in U.S. Appl. No. 15/945,313.
U.S. Notice of Allowance dated Dec. 26, 2022 issued in U.S. Appl. No. 17/723,111.
U.S. Final Office Action dated Jun. 24, 2022 issued in U.S. Appl. No. 17/723,111.
U.S. Notice of Allowance dated Sep. 12, 2024 issued in U.S. Appl. No. 18/138,334.
U.S. Final Office Action dated Jun. 5, 2024 issued in U.S. Appl. No. 18/138,334.
U.S. Non-Final Office Action dated Nov. 24, 2023 issued in U.S. Appl. No. 18/138,334.

* cited by examiner

220

ULTRASOUND SYSTEM AND SIGNAL PROCESSING UNIT CONFIGURED FOR TIME GAIN AND LATERIAL GAIN COMPENSATION

The present application is a Continuation Patent Application of U.S. patent application Ser. No. 18/138,334, filed on Apr. 24, 2023, which is a Continuation Patent Application of U.S. patent application Ser. No. 17/723,111, filed on Apr. 18, 2022, now U.S. Pat. No. 11,633,174, issued on Apr. 25, 2023, which is a Continuation Patent Application of U.S. patent application Ser. No. 15/945,313, filed on Apr. 4, 2018, which is a Continuation Patent Application of U.S. patent application Ser. No. 13/756,274, filed on Jan. 31, 2013, now U.S. Pat. No. 10,321,891, issued on Jun. 18, 2019, which is a Continuation Patent Application of U.S. patent application Ser. No. 13/184,094, filed on Jul. 15, 2011, now U.S. Pat. No. 8,403,855, issued on Mar. 26, 2013, which is a Continuation Patent Application of U.S. patent application Ser. No. 11/857,860, filed on Sep. 19, 2007, now U.S. Pat. No. 8,016,759, issued on Sep. 13, 2011, which claims priority from Korean Patent Application No. 10-2006-0123752 filed on Dec. 7, 2006, the entire subject matter of which is incorporated herein by reference.

BACKGROUND

1. Field

The present invention generally relates to an ultrasound system, and more particularly to an ultrasound system adapted to precisely and easily perform TGC (Time Gain Compensation) and LGC (Lateral Gain Compensation).

2. Background

An ultrasound system has become an important and popular diagnostic tool since it has a wide range of applications. Specifically, due to its non-invasive and non-destructive nature, the ultrasound system has been extensively used in the medical profession. Modern high-performance ultrasound systems and techniques are commonly used to produce two or three-dimensional diagnostic images of internal features of an object.

In order to transmit and receive ultrasound signals, the ultrasound system is generally provided with a probe including a wideband transducer. When the transducer is electrically stimulated, it produces ultrasound signals and transmits them into a human body. The ultrasound signals transmitted into the human body are reflected from borders between human tissues and then returned to the transducer. The returned ultrasound echo signals are converted into electric signals. Thereafter, ultrasound image data for imaging the tissues is produced by amplifying and signal-processing the echo signals.

Typically, the ultrasound system is provided with a control panel including a plurality of input units in order to perform a control function of acquiring the ultrasound image, a menu control function, a measurement and annotation function, etc. The control panel is comprised of a touch panel, an image control unit, a measurement control unit, etc. The touch panel displays menus for optimizing an ultrasound image displayed on a display unit. The menus on the touch panel can be touched and selected by a user. The image control unit controls the ultrasound image, whereas the measurement control unit measures a distance to the object, a circumference of the object, etc. As illustrated in FIG. 1, the image control unit includes a plurality of TGC control keys 11 and a plurality of LGC control keys 12. The TGC control keys 11 are used to control a gain of each echo signal based on depth of the position from which the echo signal is reflected. Further, since the echo signal is attenuated at the outer right and left sides, the LGC control keys 12 are used to control a gain of the attenuated echo signal.

In the conventional system, the TGC control keys 11 and the LGC control keys 12 are arranged on different areas of the control panel. The problem associated with such an arrangement is that the size of the control panel must be inevitably increased. Further, a user of the system suffers a great inconvenience when operating the TGC control keys 11 and the LGC control keys 12. Another problem of the conventional system is that since the TGC control keys 11 and the LGC control keys 12 are comprised of slide-type variable resistors, it is very difficult for an unskilled user to finely control TGC and LGC with the TGC control keys 11 and the LGC control keys 12.

In order to resolve the above problems, the present invention is directed to providing an ultrasound system adapted to display a setup screen used to input TGC and LGC curves on a touch panel and perform TGC and LGC based on the inputted TGC and LGC curves.

The present invention provides an ultrasound system, which comprises: a signal acquiring unit adapted to transmit an ultrasound signal to an object and acquire an echo signal reflected from the object; a signal processing unit adapted to perform TGC (Time Gain Compensation) and LGC (Lateral Gain Compensation) upon the echo signal at a coarse compensation mode based on predetermined TGC and LGC values; an image producing unit adapted to produce an ultrasound image of the object based on the TGC and LGC compensated echo signal; an input unit adapted to allow a user to provide TGC and LGC curves; and a TGC/LGC setup processor adapted to set TGC and LGC values based on the TGC and LGC curves provided by the user. The signal processing unit is further adapted to perform the TGC and LGC upon the echo signal at a fine compensation mode based on the TGC and LGC values set by the TGC/LGC setup processor.

In addition, the present invention provides an ultrasound system, which comprises: a processor adapted to configure a setup screen for display; and a touch panel adapted to display the setup screen so as to allow a user to input TGC and LGC curves. The processor is further adapted to calculate the TGC and LGC values based on the inputted TGC and the LGC curves.

BRIEF DESCRIPTION OF THE DRAWINGS

Arrangements and embodiments may be described in detail with reference to the following drawings in which like reference numerals refer to like elements and wherein.

DETAILED DESCRIPTION OF THE PRESENT INVENTION

A detailed description may be provided with reference to the accompanying drawings. One of ordinary skill in the art may realize that the following description is illustrative only and is not in any way limiting. Other embodiments of the present invention may readily suggest themselves to such skilled persons having the benefit of this disclosure.

Certain embodiments of the present invention will be explained below with reference to FIGS. 2 to 8.

Figure 1:
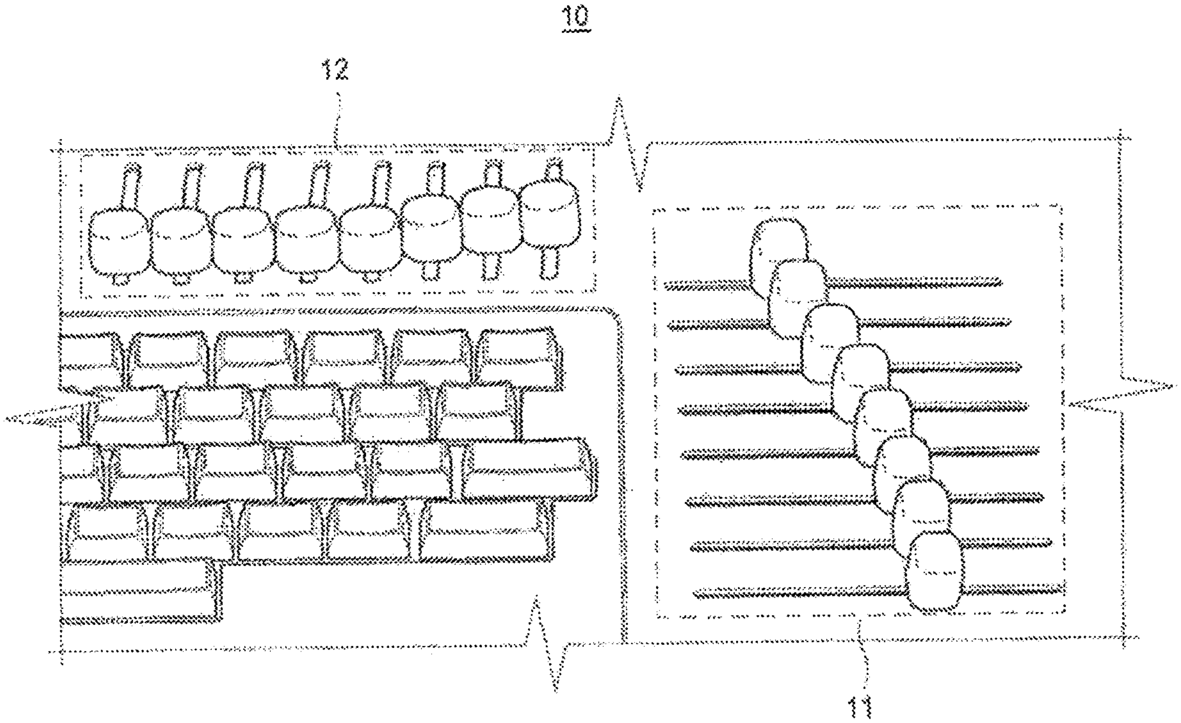
FIG. 1 is a schematic diagram illustrating conventional TGC and LGC control keys.
Figure 2:
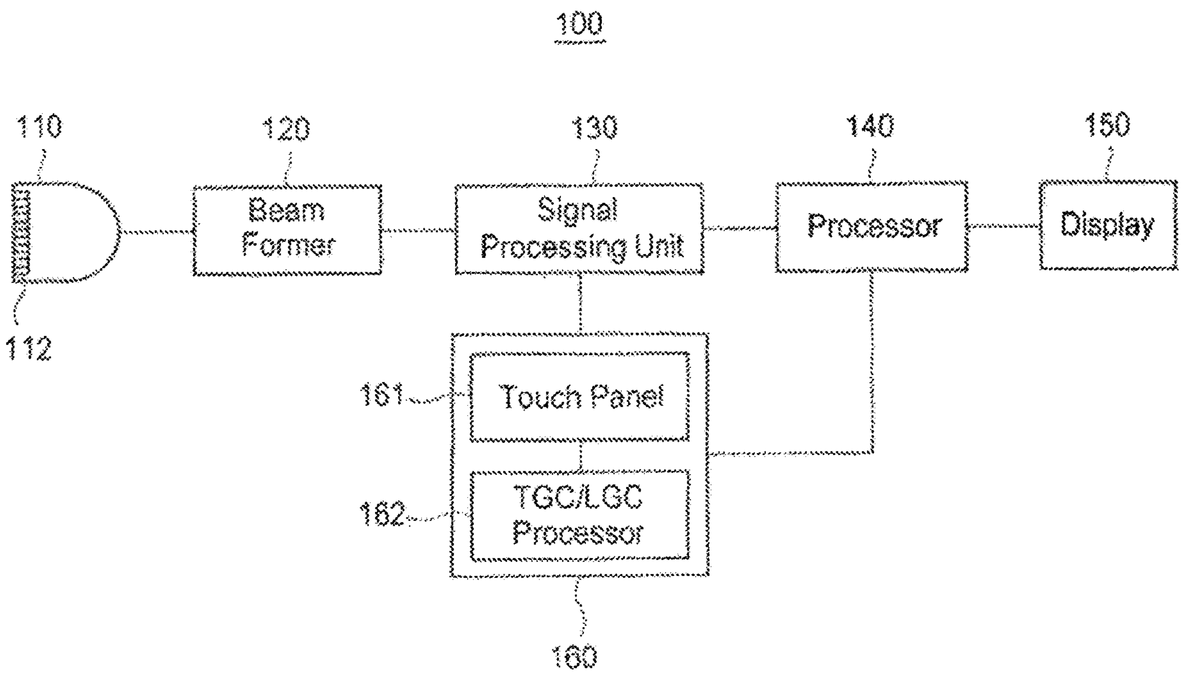
FIG. 2 is a block diagram showing a structure of an ultrasound system according to one embodiment of the present invention.
Figure 3:
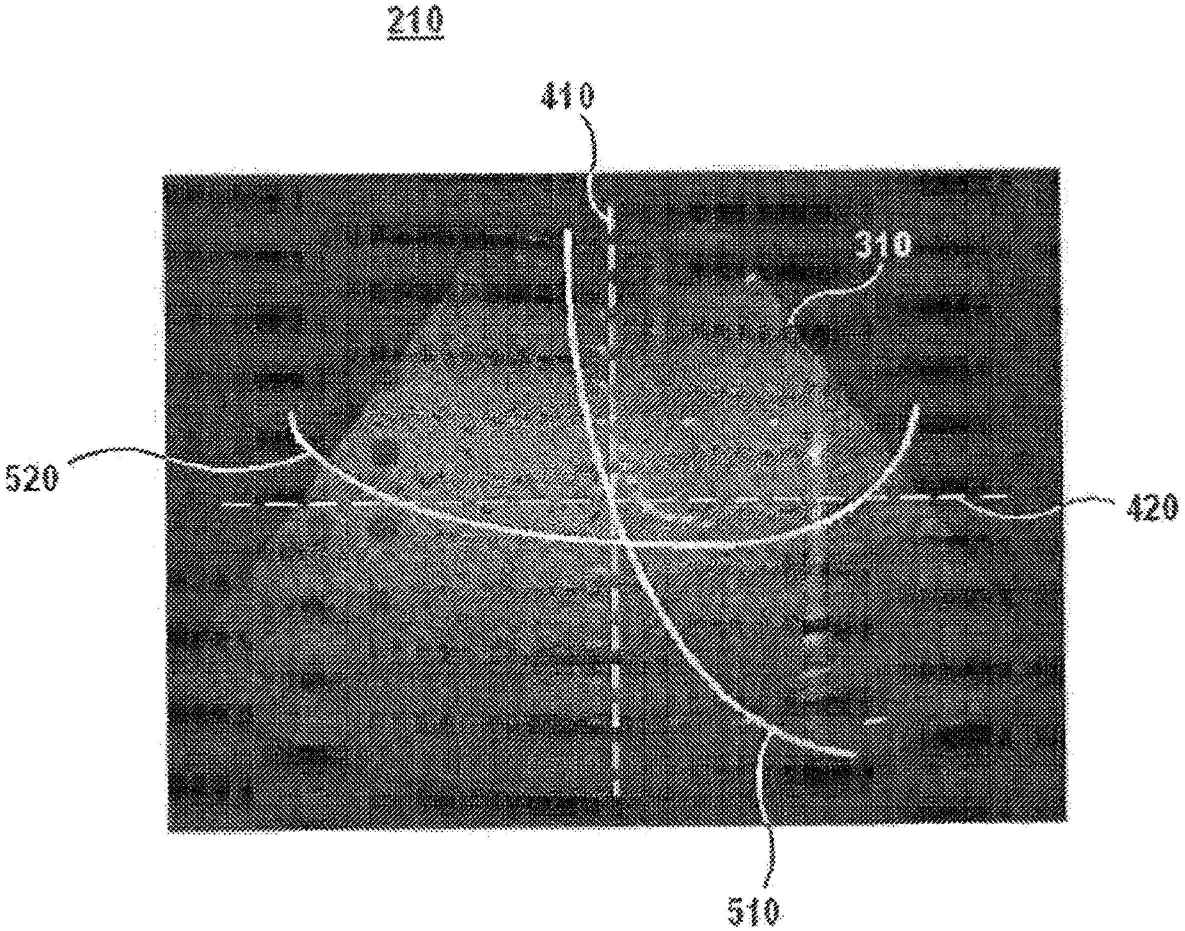
FIGS. 3 to 7 illustrate a setup screen according to one embodiment of the present.
Figure 4:
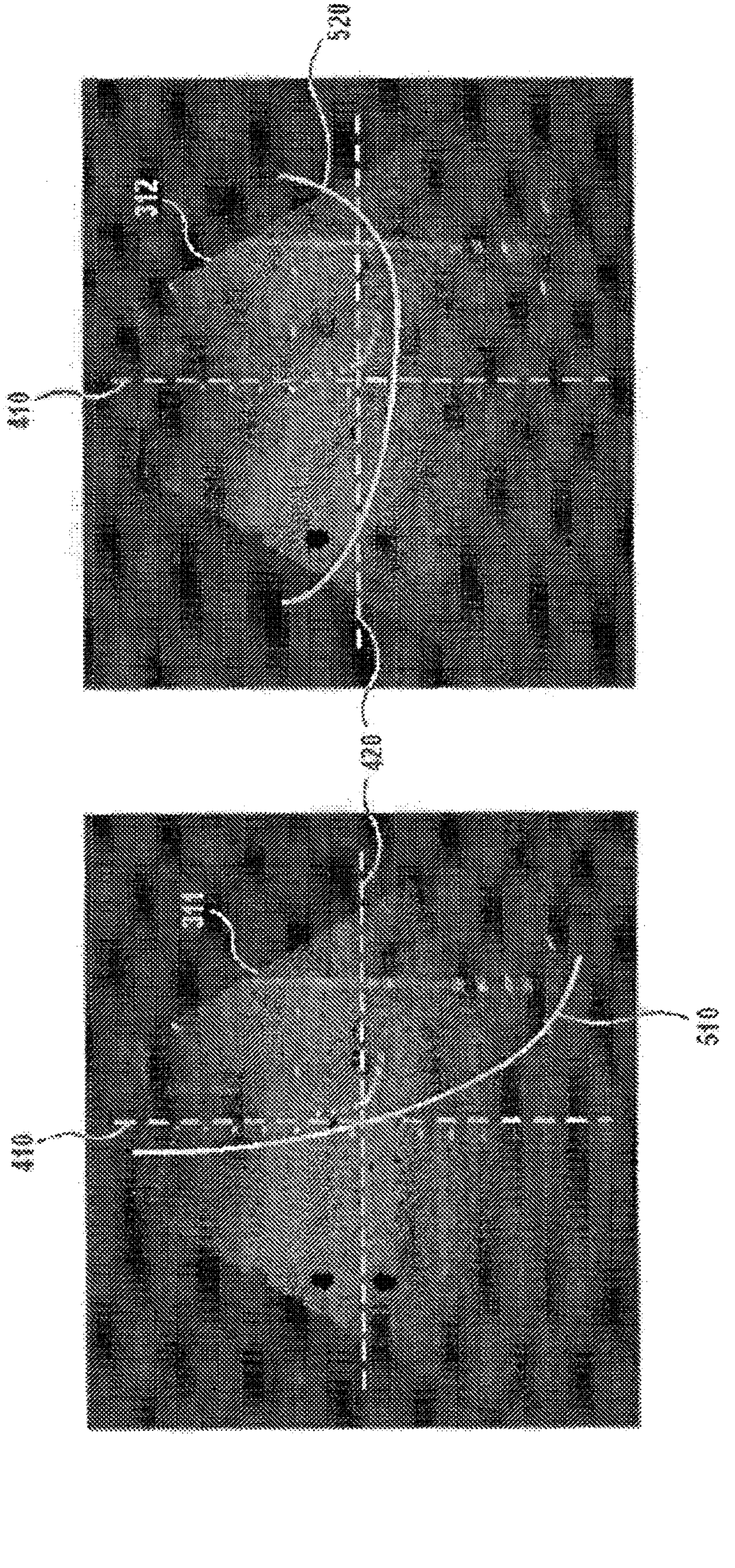
Figure 5:
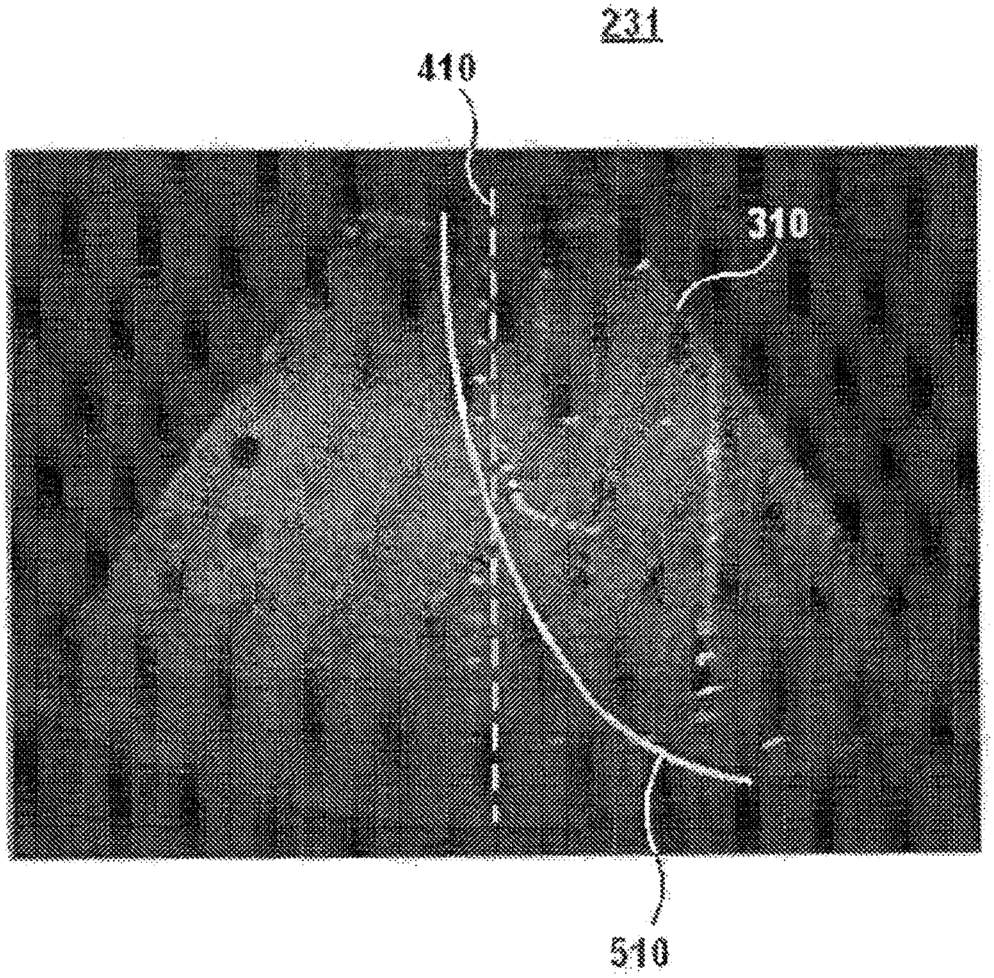
Figure 6:
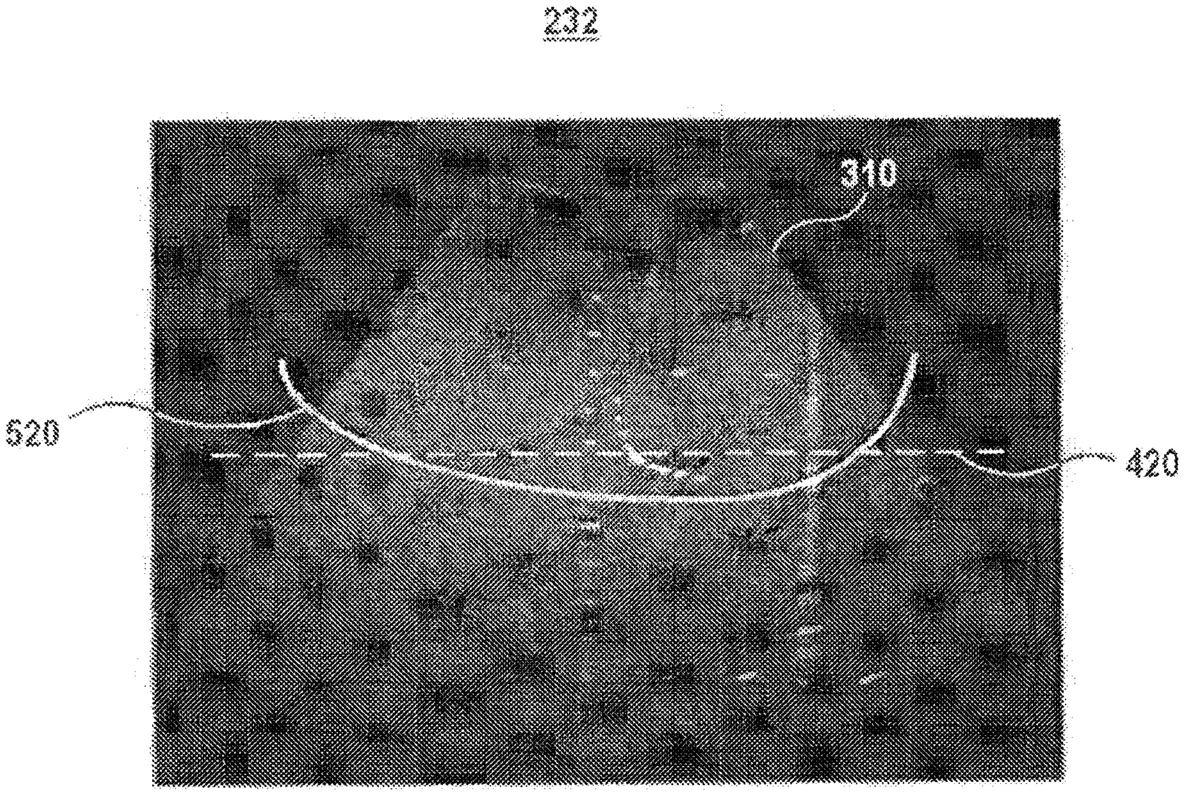
Figure 7:
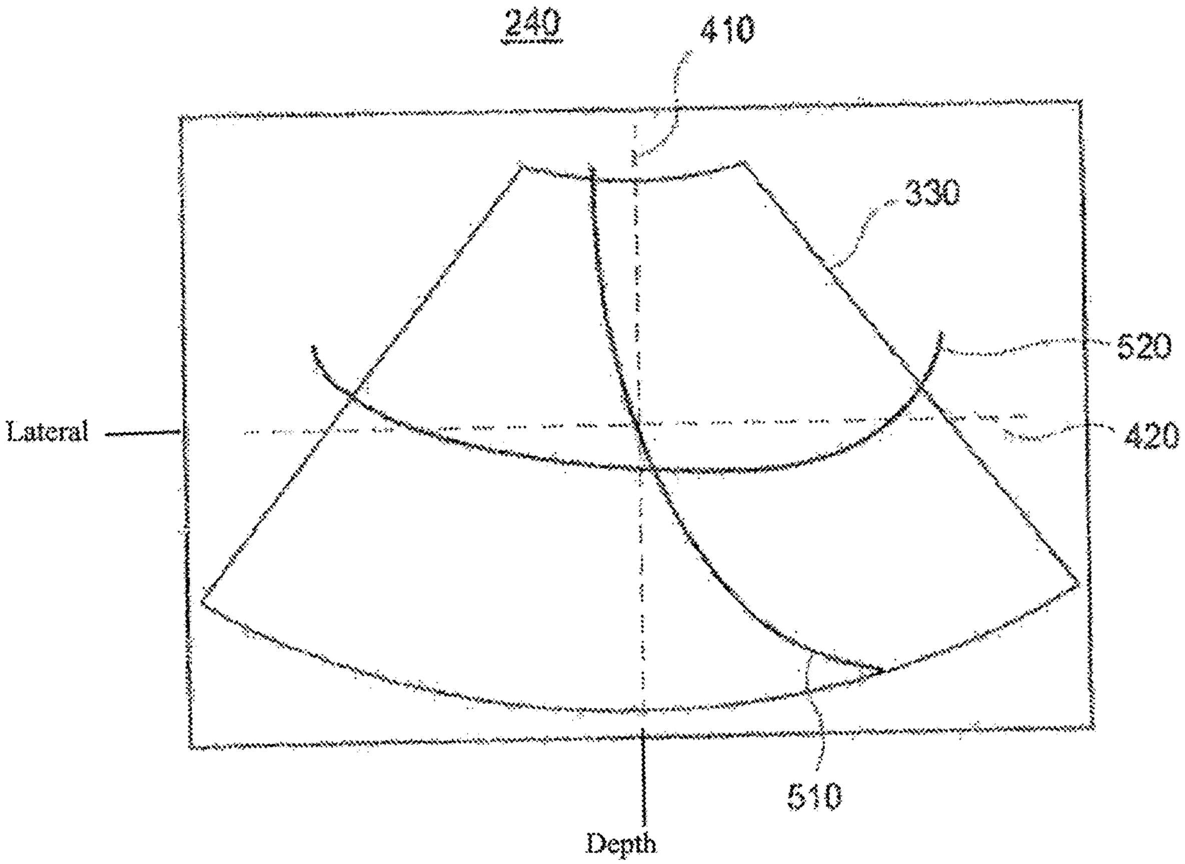

As illustrated in FIG. 2, an ultrasound system 100 comprises: a probe 110; a beam former 120; a signal processing unit 130; a processor 140; a display unit 150; and a TGC/LGC setup unit 160. The probe 110 includes a plurality of transducers 112. Each of the transducers 112 may be configured to transmit an ultrasound signal to an object and receive the ultrasound signal reflected from the object. The beam former 120 may be configured to focus the transmitted ultrasound signals from the transducers 112 on the object and collect the reflected ultrasound signals from the object to the transducers 112 together with corresponding time delay.

The signal processing unit 130 may be configured to amplify the signals collected by the beam former 120 and control gains of the amplified echo signals. Specifically, the signal processing unit 130 may be configured to perform TGC (Time Gain Compensation) and LGC (Lateral Gain Compensation) upon the echo signals based on predetermined TGC and LGC values at a coarse compensation mode (e.g., in an initial operation stage). The signal processing unit 130 may be further configured to perform TGC and LGC upon the echo signals based on TGC and LGC values calculated in a TGC/LGC setup unit 160 using a curve inputted by a user at a fine compensation mode (e.g., during operations).

The processor 140 may be configured to receive the echo signals from the signal processing unit 130 and produce an ultrasound image signal based on the echo signals. The display unit 150 may be adapted to receive the ultrasound image signal from the processor and display an ultrasound image based on the signal.

The TGC/LGC setup unit 160 may include a touch panel 161 and a TGC/LGC setup processor 162.

The touch panel 161 may be configured to display a setup screen and detect TGC/LGC curves inputted by the user on the touch panel 161 to produce a detecting signal. The touch panel 161 detects the user's input according to either the pressure sensing method or the electromagnetic induction method. The touch panel 161 may be a touch panel included in a control panel (not shown) of the ultrasound system 100. Alternatively, it may be separate and apart from the ultrasound system 100.

In one embodiment of the present invention, the touch panel 161 may be configured to display a setup screen 210 (shown in FIG. 3) including an ultrasound image 310 and first and second reference lines 410, 420. The ultrasound image 310 is based on the echo signal, the TGC and LGC of which are controlled based on the predetermined TGC and LGC values. The first and second reference lines 410, 420 may be used to detect a TGC curve 510 and a LGC curve 520 inputted by the user (i.e., to determine whether a curve inputted by the user is a TGC curve 510 or a LGC curve 520). After inputting a curve, the user can modify a portion of the curve.

In another embodiment of the present invention, the touch panel 161 may be configured to display a setup screen 220 (shown in FIG. 4) including first and second ultrasound images 311, 312 and first and second reference lines 410, 420. The first and second ultrasound images 311, 312 are based on the echo signal, the TCGC and LGC of which are controlled based on the predetermined TGC and LGC values. The first and second reference lines 410, 420 may be used to detect whether a curve inputted by the user is a TGC curve 510 or at LGC curve 520. The first ultrasound image 311 may be identical to the second initial ultrasound image 312.

In yet another embodiment of the present invention, the touch panel 161 may be configured to display a first setup screen 231 (shown in FIG. 5) including an ultrasound image 310 and a first reference line 410. The ultrasound image 310 is based on the echo signal, the TGC and LGC of which are controlled based on the predetermined TGC and LGC values. The first reference line 410 may be used to detect a TGC curve 510 inputted by the user. The touch panel may then display a second setup screen 232 (shown in FIG. 6) including the ultrasound image 310 and a second reference line 420. The second reference lines 420 may be used to detect a LGC curve 520 inputted by the user. Alternatively, the touch panel 161 may be configured to display the second setup screen 232 before the first setup screen 231.

In still yet another embodiment of the present invention, the touch panel 161 may be configured to display a setup screen 240 (shown in FIG. 7) including a virtual ultrasound image 330 and first and second reference lines 410, 420.

The TGC/LGC setup processor 162 may be configured to detect TGC and LGC curves 510, 520 inputted by the user on the touch panel 161. The TGC/LGC setup processor 162 may then calculate new TGC and LGC values m consideration of the detected TGC and LGC curves and transmit the values to the signal processing unit 130.

Figure 8:
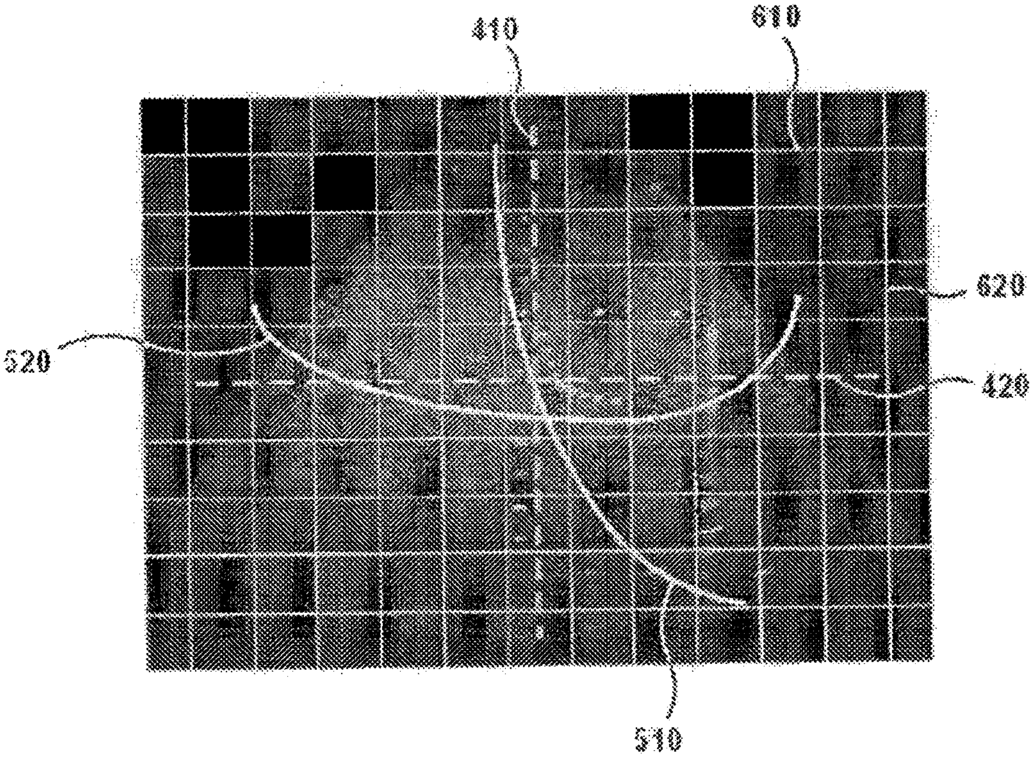
FIG. 8 illustrates an exemplary distinction between TGC and LGC curves according to one embodiment of the present invention.

In one embodiment of the present invention, as illustrated in FIG. 8, the TGC/LGC setup processor 162 may be configured to establish a first group of tines 610 and a second group of lines 620. The first group of lines 610 is perpendicular to a first reference line 410 and the lines in said group are equally spaced apart from each other. The second group of lines 620 is perpendicular to a second reference line 420 and the lines in this group are equally spaced apart from each other. If it is determined that a curve inputted by the user (such as the curve 510) intersects the first group of lines more often than the second group of lines, then the TGC/LGC setup processor 162 recognizes that the curve is a TGC curve. Alternatively, if it is determined that a curve inputted by the user (such as the curve 520) intersects the second group of lines more often than the first group of lines, then the TGC/LGC setup processor 162 recognizes that the curve is a LGC curve. The TGC/LGC setup processor 162 then calculates die new IC value corresponding to the TGC curve 510 based on the first reference line 410. It also calculates the LGC value corresponding to the LGC curve 520 based on the second reference line 420. The TGC value and the LGC value are transmitted to the signal processing unit 130.

The present invention allows the user to accurately control the TGC and LGC by using the TGC and LGC curves inputted into the touch panel, thereby improving operational accuracy and time. Further, the present invention reduces the size of the control panel to thereby improve the spatial efficiency.

Although the present invention has been described with reference to a number of preferred embodiments thereof, it should be understood that numerous other modifications and embodiments can be devised by those skilled in the art that will fall within the spirit and scope of the principles of this disclosure. More particularly, numerous variations and modifications are possible in the component parts and/or arrangements of the subject combination arrangement within the scope of the disclosure, the drawings and the appended claims. In addition to variations and modifications in the component parts and/or arrangements, alternative uses will also be apparent to those skilled in the art.

What is claimed is:

1. An ultrasound system, comprising:

a plurality of transducers configured to transmit an ultrasound signal to an object and receive echo signal reflected from the object;

a beam former configured to focus the transmitted ultrasound signal and collect the echo signal with corresponding time delay; and a processor configured to:

display at least one reference line on a touch panel, receive a touch input through the touch panel, wherein the touch input intersects with the displayed at least one reference line, and comprises a plurality of touch input points including a first touch input point and a second touch input point, determine a first time gain compensation (TGC) value and a second TGC value at two different depths corresponding to the first touch input point and the second touch input point respectively, perform compensation on the echo signal based on the determined first TGC value and the second TGC value, and generate an ultrasound image of the object based on the compensated echo signal, wherein the first touch input point and the second touch input point for setting the first TGC value and the second TGC value are received via a single touch input forming a single curve, and wherein the single curve is displayed on the touch panel, and the displayed at least one reference line and the displayed single curve are displayed as different types of lines.

2. The ultrasound system of claim 1, wherein the processor is configured to amplify the collected echo signals and control gains of the amplified echo signals based on the first TGC value and the second TGC value to perform compensation on the echo signal.

3. The ultrasound system of claim 1, wherein the at least one reference line comprises a plurality of reference lines.

4. The ultrasound system of claim 1, wherein the compensation on the echo signal corresponds to a time gain compensation (TGC), and the single curve corresponds to a TGC curve.

5. The ultrasound system of claim 1, wherein the processor is further configured to calculate the first TGC value and the second TGC value based on intersections between the at least one reference line and the single curve to determine the first TGC value and the second TGC value.

6. The ultrasound system of claim 1, wherein the processor is further configured to display an ultrasound image based on current TGC values, and update the displayed ultrasound image based on the determined first TGC value and the determined second TGC value.

7. The ultrasound system of claim 1, wherein the at least one reference line is displayed as a dotted line with first thickness.

8. The ultrasound system of claim 1, wherein the at least one reference line is displayed as a solid line with first thickness.

9. A method of controlling an ultrasound system comprising:

transmitting an ultrasound signal to an object and receiving echo signal reflected from the object;

focussing the transmitted ultrasound signal and collecting the echo signal with corresponding time delay;

displaying at least one reference line;

receiving a touch input, wherein the touch input intersects with the displayed at least one reference line, and comprises a plurality of touch input points including a first touch input point and a second touch input point;

determining a first time gain compensation (TGC) value and a second TGC value at two different depths corresponding to the first touch input point and the second touch input point respectively, performing compensation on the echo signal based on the determined first TGC value and the second TGC value, and generating an ultrasound image of the object based on the compensated echo signal, wherein the first touch input point and the second touch input point for setting the first TGC value and the second TGC value are received via a single touch input forming a single curve, and wherein the single curve is displayed, and the displayed at least one reference line and the displayed single curve are displayed as different types of lines.

10. The method of claim 9, wherein the performing compensation on the echo signal comprises amplifying the collected echo signals and controlling gains of the amplified echo signals based on the first TGC value and the second TGC value.

11. The method of claim 9, further comprising displaying the at least one reference line and the single curve on a touch panel which receives the touch input.

12. The method of claim 9, wherein the at least one reference line comprises a plurality of reference lines.

13. The method of claim 9, wherein the compensation on the echo signal corresponds to a time gain compensation (TGC), and the single curve corresponds to a TGC curve.

14. The method of claim 9, wherein the determining the first TGC value and the second TGC value comprises calculating the first TGC value and the second TGC value based on intersections between the at least one reference line and the displayed single curve.

15. The method of claim 9, further comprising displaying an ultrasound image based on current TGC values, and updating the displayed ultrasound image based on the determined first TGC value and the determined second TGC value.

16. The method of claim 9, wherein the at least one reference line is displayed as a dotted line with first thickness.

17. The method of claim 9, wherein the at least one reference line is displayed as a solid line with first thickness.

* * * * *